(12) United States Patent
Sharma

(10) Patent No.: US 12,029,438 B2
(45) Date of Patent: *Jul. 9, 2024

(54) MEASUREMENT MODULE OF A SURGICAL SYSTEM FOR DETERMINING DRILL BREAKTHROUGH

(71) Applicant: Stryker Corporation, Kalamazoo, MI (US)

(72) Inventor: Rahul Sharma, Gurgaon (IN)

(73) Assignee: Stryker Corporation, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/074,352

(22) Filed: Dec. 2, 2022

(65) Prior Publication Data

US 2023/0120811 A1    Apr. 20, 2023

Related U.S. Application Data

(63) Continuation of application No. 16/784,878, filed on Feb. 7, 2020, now Pat. No. 11,517,326.
(Continued)

(51) Int. Cl.
*A61B 17/16* (2006.01)
*A61B 17/00* (2006.01)

(52) U.S. Cl.
CPC ...... *A61B 17/1626* (2013.01); *A61B 17/1615* (2013.01); *A61B 17/1628* (2013.01);
(Continued)

(58) Field of Classification Search
CPC ... A61B 17/1626; A61B 17/32; A61B 17/107; A61B 17/1615; A61B 17/1628; A61B 90/00; G01B 7/14
See application file for complete search history.

(56) References Cited

U.S. PATENT DOCUMENTS 1,831,813 A   11/1931   Levedahl
3,804,544 A    4/1974   Adams
(Continued)

FOREIGN PATENT DOCUMENTS

WO   2017040783 A1   3/2017
WO   2017083989 A1   5/2017
(Continued)

*Primary Examiner* — Nathaniel C Chukwurah
(74) *Attorney, Agent, or Firm* — Howard & Howard Attorneys PLLC

(57) ABSTRACT

A handheld surgical instrument includes a motor that transmits rotational movement to a drill bit of the handheld surgical instrument. The drill bit extends through a depth measurement module with a depth measurement extension, and a cannula, which extends forward from the drill to measure bore depth. The depth measurement extension is moveably mounted to the drill so as to extend into the rotor bore of the motor. As the drill advances forward, the depth measurement extension remains static. As a result of the advancement of the drill, the rotor extends over the proximal end of the depth measurement extension. A controller is configured to determine a breakthrough time and a breakthrough displacement of the drill bit based on displacement data and derived signals. The controller is further configured to determine a proper length of a screw to be used in a fixation surgical procedure based on the displacement data.

20 Claims, 11 Drawing Sheets

Related U.S. Application Data

(60) Provisional application No. 62/802,285, filed on Feb. 7, 2019.

(52) U.S. Cl.
CPC ............. *A61B 2017/00132* (2013.01); *A61B 2017/00221* (2013.01); *A61B 2560/0431* (2013.01); *A61B 2560/0462* (2013.01)

(56) References Cited

U.S. PATENT DOCUMENTS

| | | | |
|---|---|---|---|
| 6,665,948 B1 | 12/2003 | Kozin et al. | |
| 6,776,562 B2 | 8/2004 | Morrison et al. | |
| 7,111,411 B2 | 9/2006 | Knopfle et al. | |
| 7,165,336 B2 | 1/2007 | Kim | |
| 7,220,088 B2 | 5/2007 | Ferrari et al. | |
| 7,676,943 B2 | 3/2010 | Kim et al. | |
| 8,115,945 B2 | 2/2012 | Plewnia | |
| 8,460,297 B2 | 6/2013 | Watlington et al. | |
| 8,511,945 B2 | 8/2013 | Apkarian et al. | |
| 8,734,153 B2 | 5/2014 | Arzanpour et al. | |
| 8,821,493 B2 | 9/2014 | Anderson | |
| 8,894,654 B2 | 11/2014 | Anderson | |
| 8,911,448 B2 | 12/2014 | Stein | |
| 8,970,207 B2 | 3/2015 | Baumgartner | |
| 9,204,885 B2 | 12/2015 | McGinley et al. | |
| 9,237,885 B2 | 1/2016 | Stein et al. | |
| 9,345,552 B2 * | 5/2016 | Janik | A61B 34/75 |
| 9,358,016 B2 | 6/2016 | McGinley et al. | |
| 9,370,372 B2 | 6/2016 | McGinley et al. | |
| 9,826,984 B2 | 11/2017 | McGinley et al. | |
| 9,828,157 B2 | 11/2017 | Roesler | |
| 9,999,469 B2 | 6/2018 | Roesler | |
| 10,028,801 B1 | 7/2018 | McGinley et al. | |
| 10,321,920 B2 * | 6/2019 | McGinley | A61B 17/1633 |
| 10,398,453 B2 | 9/2019 | McGinley et al. | |
| 10,420,625 B2 | 9/2019 | Suzuki et al. | |
| 11,517,326 B1 * | 12/2022 | Sharma | A61B 17/1626 |
| 2003/0049082 A1 | 3/2003 | Morrison et al. | |
| 2009/0245956 A1 | 10/2009 | Apkarian et al. | |
| 2009/0326537 A1 | 12/2009 | Anderson | |
| 2011/0245833 A1 * | 10/2011 | Anderson | B23B 49/02 606/80 |
| 2013/0060278 A1 * | 3/2013 | Bozung | A61B 17/1675 606/205 |
| 2013/0096574 A1 * | 4/2013 | Kang | A61B 34/30 606/130 |
| 2014/0107471 A1 * | 4/2014 | Haider | A61B 5/1076 606/82 |
| 2014/0371752 A1 | 12/2014 | Anderson | |
| 2015/0066030 A1 | 3/2015 | McGinley et al. | |
| 2015/0066035 A1 | 3/2015 | McGinley et al. | |
| 2015/0066036 A1 | 3/2015 | McGinley et al. | |
| 2015/0066037 A1 | 3/2015 | McGinley et al. | |
| 2015/0066038 A1 | 3/2015 | McGinley et al. | |
| 2015/0080966 A1 | 3/2015 | Anderson | |
| 2015/0182285 A1 * | 7/2015 | Yen | A61B 17/1626 606/86 R |
| 2016/0120553 A1 | 5/2016 | Xie | |
| 2016/0128704 A1 * | 5/2016 | McGinley | A61B 17/17 606/86 R |
| 2016/0244234 A1 | 8/2016 | Mayer et al. | |
| 2017/0143396 A1 | 5/2017 | McGinley et al. | |
| 2018/0185034 A1 | 7/2018 | McGinley et al. | |
| 2019/0040810 A1 | 2/2019 | Andersson et al. | |
| 2021/0307764 A1 | 10/2021 | Windolf et al. | |

FOREIGN PATENT DOCUMENTS

| | | |
|---|---|---|
| WO | 2017083992 A1 | 5/2017 |
| WO | 2017139674 A1 | 8/2017 |
| WO | 2017172949 A1 | 10/2017 |

* cited by examiner

MEASUREMENT MODULE OF A SURGICAL SYSTEM FOR DETERMINING DRILL BREAKTHROUGH

CROSS-REFERENCE TO RELATED APPLICATION

The subject patent application is a continuation patent application of U.S. patent application Ser. No. 16/784,878 filed on Feb. 7, 2020, now U.S. Pat. No. 11,517,326 issued on Dec. 6, 2022, which claims priority to and all of the benefits of U.S. Provisional Patent Application No. 62/802,285, filed on Feb. 7, 2019, the disclosures of which are hereby incorporated by reference.

FIELD OF DISCLOSURE

U.S. Patent Classification (USPC) 600.080 (REAMER OR DRILL) and Cooperative Patent Classification (CPC) A61B17/1628 (DRILL HANDPIECES). This disclosure relates generally to a system and method for drilling through bone. More specifically, this disclosure relates to a system and method for determining a time breakthrough during a surgical drilling process.

BACKGROUND OF THE DISCLOSURE

A common practice in orthopedic surgery is to use a plurality of different surgical tools to repair bone trauma, joint damage due to wear, birth defects, damage due to disease, and a like. A non-limiting example of such a tool is a rotary cutting handheld surgical instrument, such as a drill. These handheld surgical instruments are used to create bore holes for many different purposes, such as place screws to repair a bone fracture trauma with screws to hold a fixator in place. An important part of these surgical procedures is to determine the proper length of screws to use.

A typical method of bore-hole depth determination uses a separate device in the form of a depth gauge that is introduced into the patient's body to measure the depth of the bore hole. The two significant disadvantages to this protocol are 1) introducing another surgical instrument into the patient's body where maintaining sterility; and 2) the increasing the surgical time leaving the patient exposed to the ambient environment.

SUMMARY OF THE DISCLOSURE

In a feature, a handheld surgical instrument is described. The handheld surgical instrument includes a housing, a motor positioned within the housing, a depth measurement extension that is operably coupled to the housing, and a displacement sensor that is operably connected to the depth measurement extension such that the displacement sensor is configured to provide a displacement signal over a first time interval. The first time interval is bounded by an initial time and a final time with the first time interval corresponding to a drilling process. The handheld surgical instrument also includes a controller that is operably connected to the displacement sensor to receive the displacement signal and a memory device, that is operably connected to the controller, configured to store data. The controller is configured to determine a preceding velocity-related signal from the displacement signal over a second time interval, where the second time interval is at least a portion of the first time interval. The controller is further configured to determine a first acceleration-related signal over a third time interval based on the displacement signal, the third time interval being within the first time interval, where the third time interval is after the second time interval. The controller is further configured to determine a preceding velocity factored acceleration-related signal for the third time interval based on the first acceleration-related signal and the preceding velocity-related signal. The controller is further configured to determine a breakthrough time of a drill bit through a distal cortical wall of a bone within the first time interval based on the preceding velocity factored acceleration-related signal. The controller is further configured to determine a breakthrough displacement from the displacement signal at the breakthrough time.

In a feature, a handheld surgical instrument is described. The handheld surgical instrument includes a housing, a motor positioned within the housing, a depth measurement extension that is operably coupled to the housing, a displacement sensor that is operably connected to the depth measurement extension such that the displacement sensor is configured to provide a displacement signal over a first time interval, the first time interval being bounded by an initial time and a final time with first time interval corresponding to a drilling process. The handheld surgical instrument also includes a controller, that is operably connected to the displacement sensor to receive the displacement signal and a memory device, that is operably connected to the controller, configured to store data. The controller is configured to determine a preceding velocity-related signal from the displacement signal over a second time interval, where the second time interval is at least a portion of the first time interval. The controller is further configured to determine a succeeding velocity-related signal over a third time interval, where the third time interval being within the first time interval, the second time interval preceding the third time interval. The controller is further configured to determine a first acceleration-related signal over a fourth time interval based on the displacement signal, where the fourth time interval is at least a portion of the second time interval and at least a portion of the third time interval. The controller is further configured to determine a preceding velocity acceleration-related signal over the fourth time interval based on the preceding velocity-related signal and the first acceleration-related signal. The controller is further configured to determine a soft-bone factored acceleration signal for the fourth time interval based on the preceding velocity acceleration-related signal over the second time interval and the succeeding velocity-related signal over the third time interval. The controller is further configured to determine a breakthrough time of a drill bit through a distal cortical wall of a bone within the first time interval based on the soft-bone factored acceleration signal. The controller is further configured to determine a breakthrough displacement from the displacement signal at the breakthrough time.

In a feature, a handheld surgical instrument system is described. The handheld surgical instrument system includes a housing, a motor positioned within the housing a depth measurement extension that is operably coupled to the housing, and a displacement sensor operably connected to the depth measurement extension such that the displacement sensor is configured to provide a displacement signal over a first time interval, the first time interval being bounded by an initial time and a final time, the first time interval corresponding to a drilling process. The handheld surgical instrument system also includes a controller that is operably connected to the displacement sensor to receive the displacement signal. The controller is configured to determine a preceding velocity-related signal from the displacement signal over a second time interval, where the second time interval is at least a portion of the first time interval. The controller is further configured to determine a succeeding velocity-related signal over a third time interval based on the displacement signal, the third time interval being within the first time interval, the second time interval preceding the third time interval. The controller is further configured to determine at least one forward drilling time interval within the first time interval, where the displacement signal is greater than a previous maximum displacement within the first time interval. The controller is further configured to determine a first acceleration-related signal within a fourth time interval, the fourth time interval including at least a portion of the second time interval and the third time interval based on the displacement signal, wherein the fourth time interval includes only the at least one forwarding drilling time interval. The controller is further configured to determine a preceding velocity factored acceleration-related signal for the fourth time interval based on the first acceleration-related signal and the preceding velocity-related signal. The controller is further configured identify an acceleration cycle block within a portion of first acceleration-related signal, the acceleration cycle block corresponding to a fifth time interval where increasing acceleration-related signal values precede decreasing acceleration related signal values. The controller is further configured determine a maximum acceleration in the acceleration cycle block within the fifth time interval. The controller is further configured determine a soft-bone factored acceleration signal for the fifth time interval based on the preceding velocity factored acceleration-related signal and the succeeding velocity-related signal at maximum acceleration. The controller is further configured determine a maximum soft-bone factored acceleration within the fourth time interval. The controller is further configured determine a breakthrough time of a drill bit through a distal cortical wall of a bone within the first time interval as the breakthrough time corresponding to the maximum soft-bone factored acceleration. The controller is further configured determine a bore hole depth from a starting displacement from the displacement signal and a breakthrough displacement from the displacement signal at the breakthrough time. The controller is further configured determine a screw length based on the bore hole depth. The handheld surgical instrument system further includes a display that is operably connected to the controller and configured to output the screw length.

BRIEF DESCRIPTION OF THE DRAWINGS

The novel features of this disclosure are pointed out with particularity in the claims. However, the features set out above and additional features and advantages are best understood from the following Detailed Description, taken in conjunction with the accompanying drawings in which:

DETAILED DESCRIPTION

The drill in this disclosure is designed so that a controller determines an accurate bore-depth by precisely determining the drill breakthrough of the distal cortical wall from displacement signal data collected during the drilling process. The controller of this drill implements a set of algorithms to determine the bore-hole depth. This allows the surgeon to determine a correct the screw length without using a second device, which may compromise the sterility of the procedure and/or extend procedure times.

Figure 4:
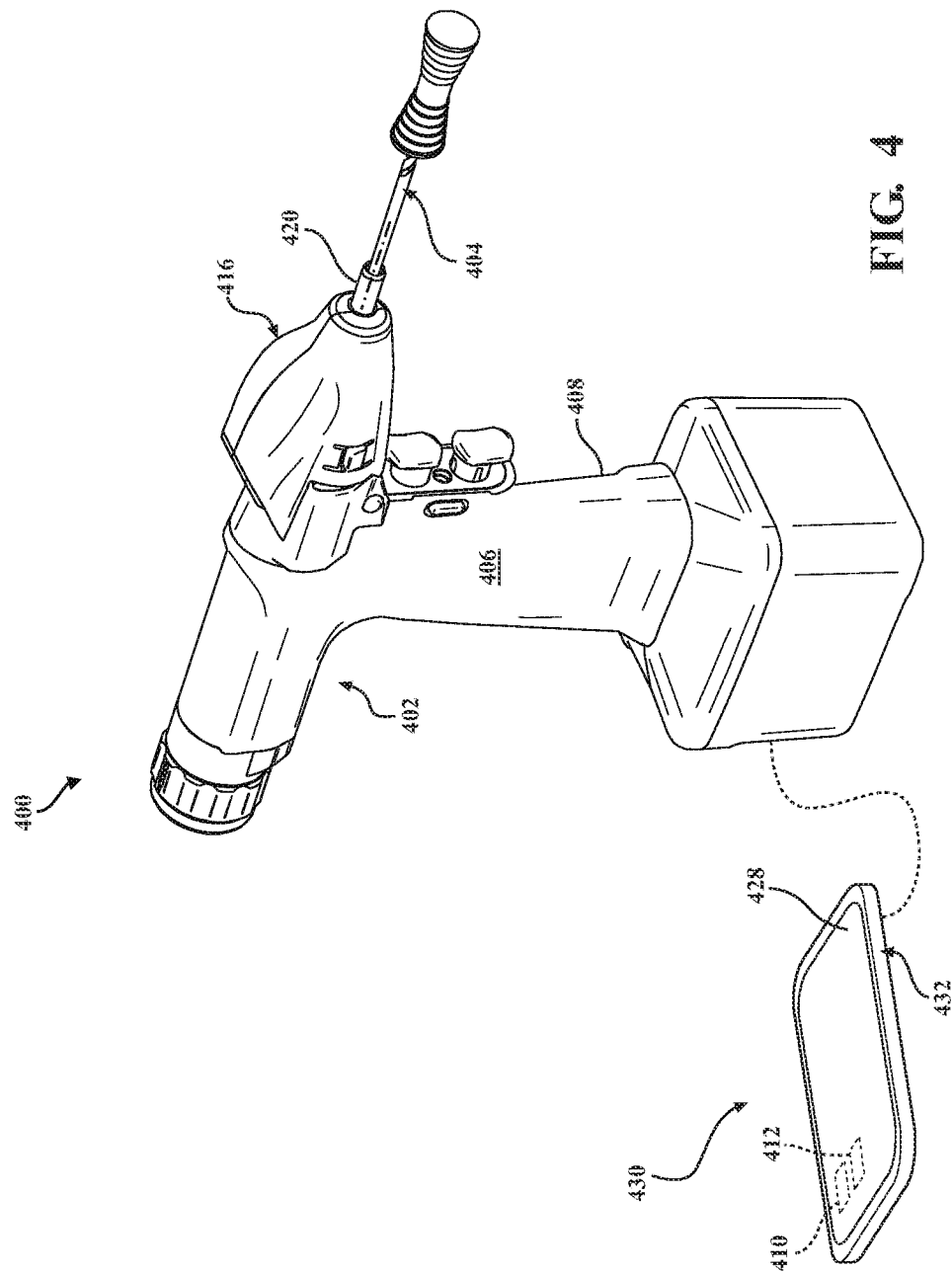
FIG. 4 is a perspective view of a system for drilling a bone including a surgical handpiece and a remote device.
Figure 5:
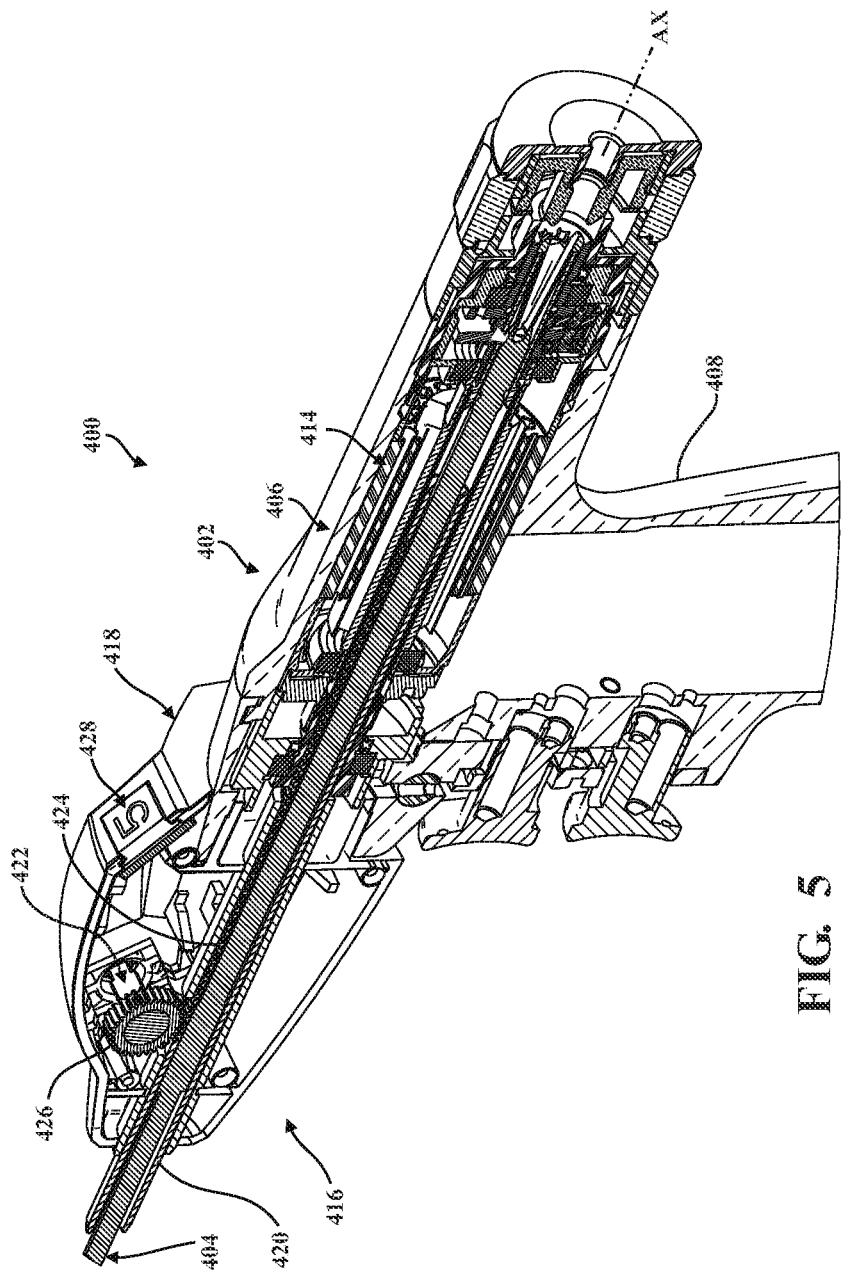
FIG. 5 is a cross-sectional and partial perspective view of the system of FIG. 4.

FIGS. 4 and 5 show a handheld surgical system 400 for use in orthopedic surgical procedures. The handheld surgical system 400 comprises a handheld surgical instrument 402, and a cutting tool 404, such as a drill bit. The handheld surgical system 400 is configured to determine a depth of a bore that is drilled by the cutting tool 404. The system may also be configured to determine a suitable screw length for bone fixation. The screw length determination may be made immediately after the bone drilling process has completed.

Figure 6:
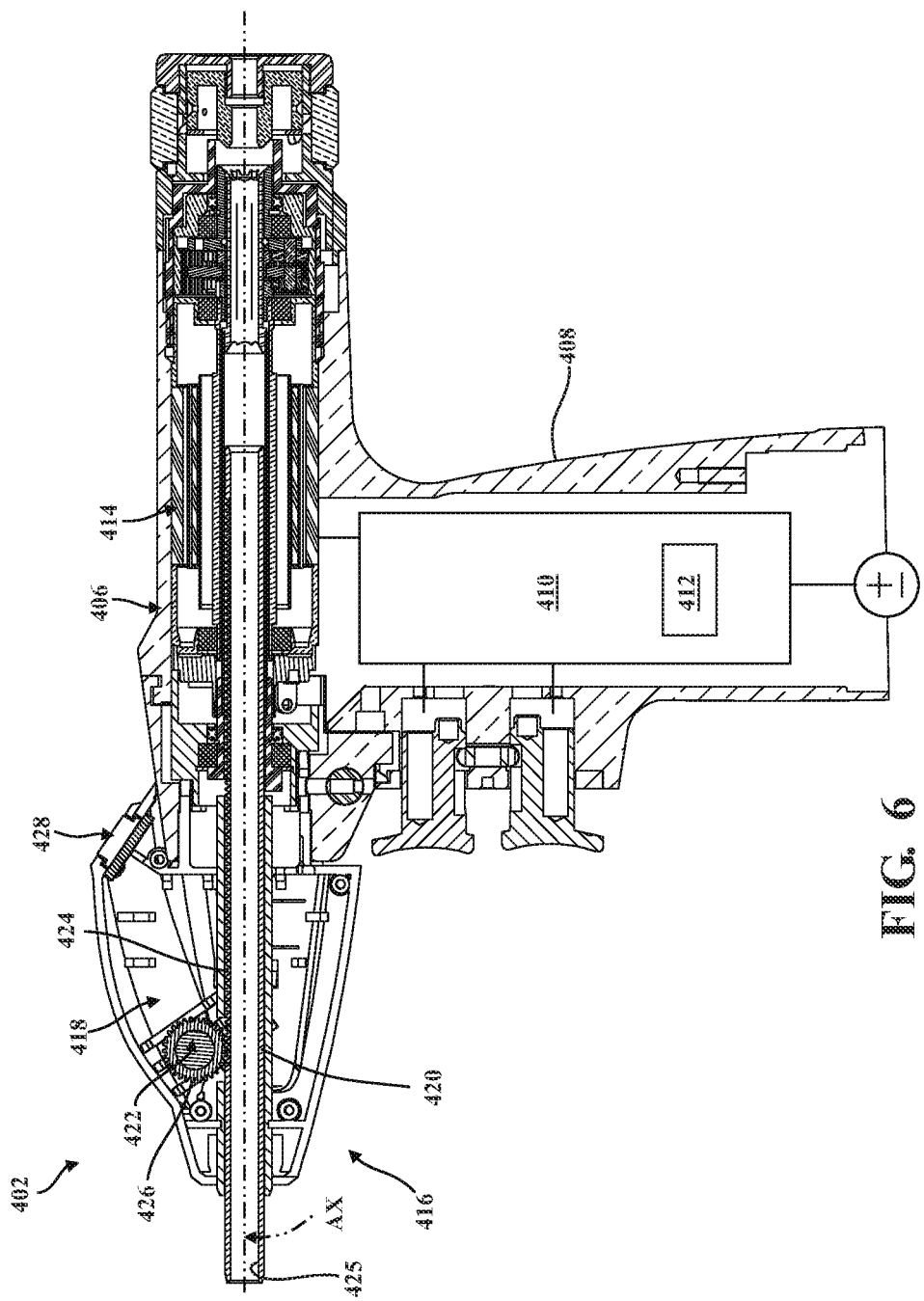
FIG. 6 is a cross-sectional view of the surgical handpiece and the depth measurement module of FIG. 4.

The handheld surgical instrument 402 may comprise a housing 406, and a motor 414 disposed within the housing. Those skilled in the art will appreciate that the housing 406 is not limited to having a pistol grip 408. FIGS. 5 and 6 show a motor 414 positioned along the proximal/distal axis AX within the housing 406, but other motor positions are contemplated. The motor 414 can be electric, pneumatic, or hydraulic.

A depth measurement module 416 may be releasably coupled to the housing 406 or may be integrally formed with the housing 406. The depth measurement module 416 may comprise a distinct housing, a module housing 418. The depth measurement module 416 may be constructed in a manner to minimize the obstruction of the surgeon's view of the surgical site. The depth measurement module may further comprise a displacement sensor 422 that is operably connected to a depth measurement extension 420. In the illustrated example, the depth measurement extension 420 is a cannula. The displacement sensor 422 is configured to output a displacement signal as the depth measurement extension 420 moves relative to the handheld surgical instrument 402. In some configurations, the depth measurement extension 420 has an inner surface 425 that is disposed over a cutting tool 404. Although, in this example, the depth measurement extension 420 is positioned concentrically over the cutting tool 404, in an alternative configuration, the depth measurement extension 420 and the cutting tool 404 do not have to be positioned concentrically.

In one configuration, the depth measurement module 416 may further comprise a rotatable gear 426. In such a configuration, the depth measurement extension 420 has a set of rack teeth 424 that are longitudinally disposed over at least a portion of its length which engage the teeth on the rotatable gear 426 by meshing with each other. The rotatable gear 426 which is functionally coupled to the displacement sensor 422, is operated by any axial movement of the depth measurement extension 420 through the engagement of the rack teeth 424 and teeth on the rotatable gear 426. In this non-limiting example, the displacement sensor 422 is a potentiometer. Other types of sensors can be used, for instance, an optical sensor, and LVDT sensor, etc.

Figure 9:
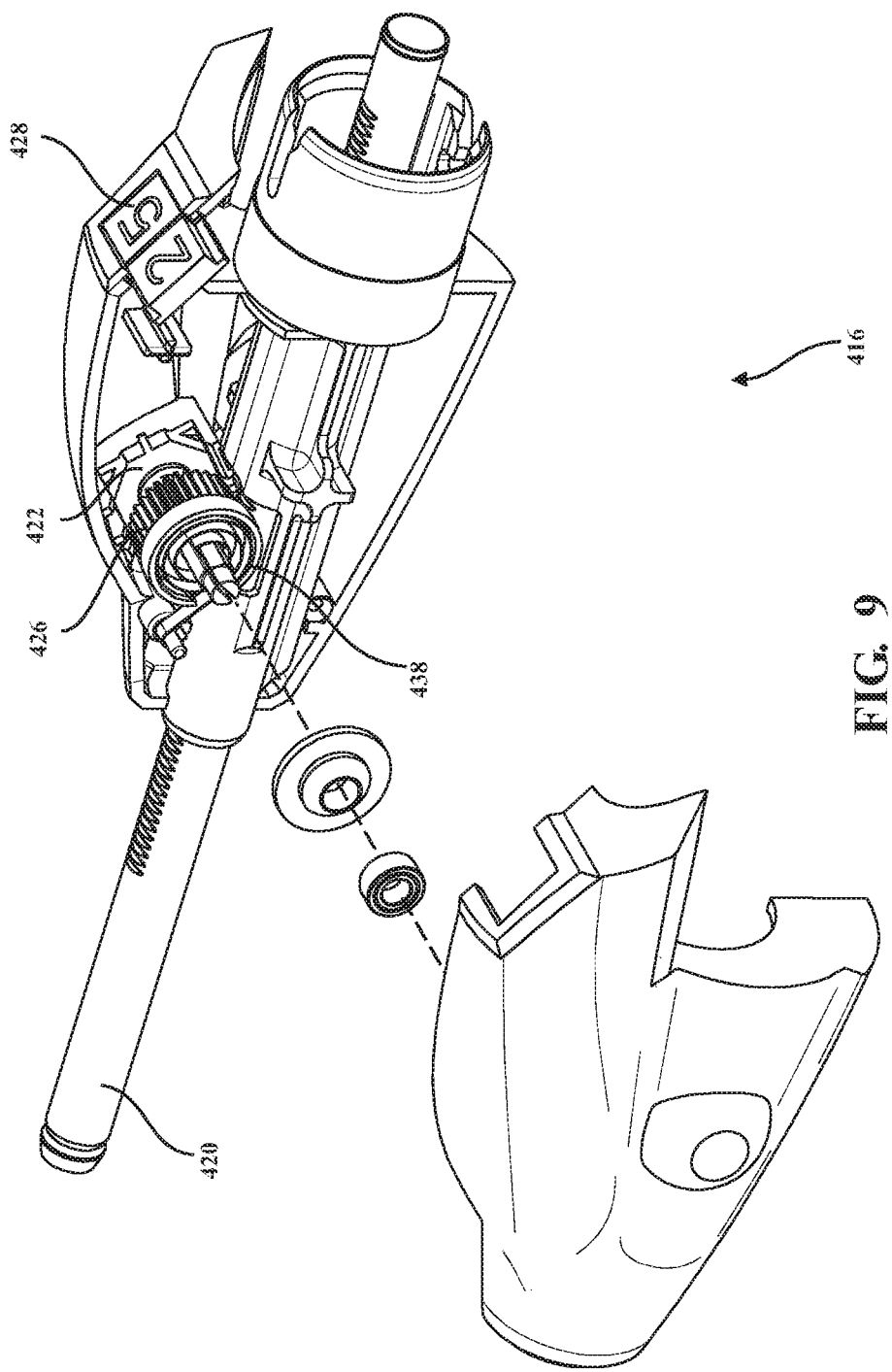
FIG. 9 is a partially exploded view of the of the depth measurement module of FIGS. 7 and 8.

In order to ensure that there is proper function of the depth measurement extension 420 and the displacement sensor 422, the depth measurement extension 420 may be biased towards an extended position. Through this bias, the distal end of the depth measurement extension 420 always maintains contact with the proximal surface of the bone to be drilled, or the plate/implant which abuts the bone to be drilled. In the illustrated example, referring to FIG. 9, this bias is achieved by use of a spring 438 that biases the rotatable gear 426 in such a way as to rotate the gear in the direction to extend the depth measurement extension 420 distally out of the module housing 418. However, other ways of biasing the depth measure extension 420 relative to the handheld surgical instrument 402 are contemplated.

Figure 7:
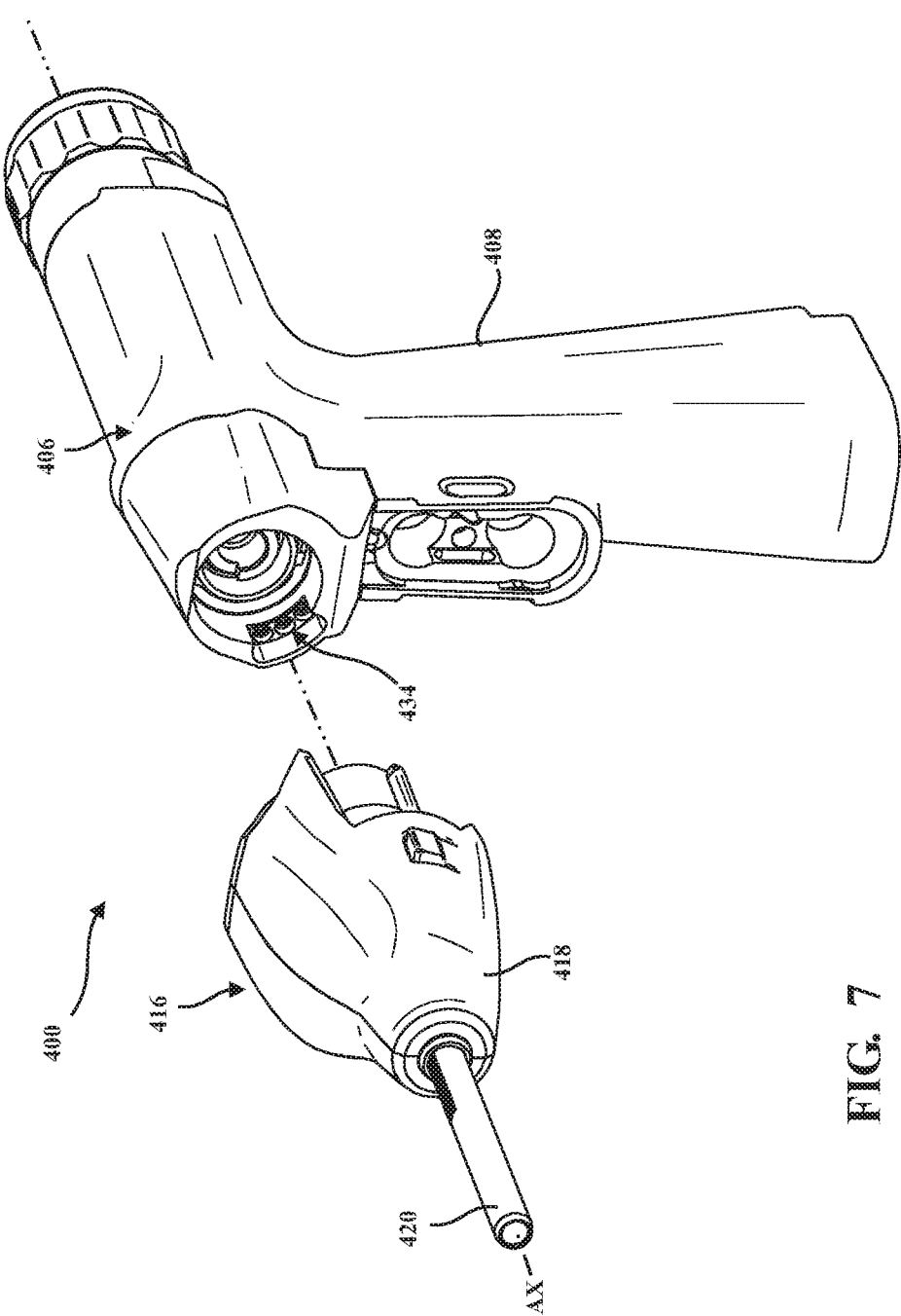
FIG. 7 is a perspective view of the system of FIG. 4 with the depth measurement module separated from the surgical handpiece.
Figure 8:
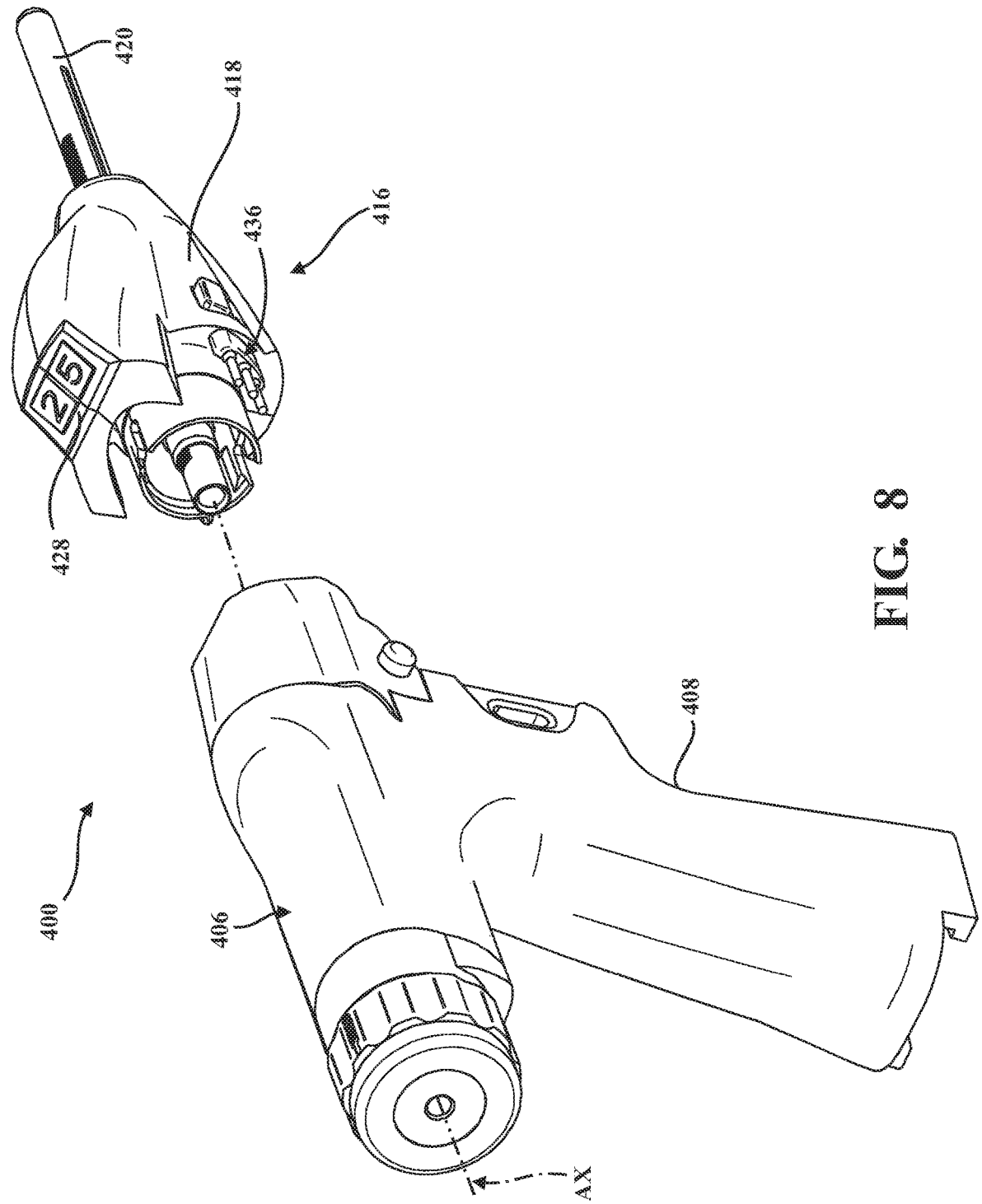
FIG. 8 is another perspective view of the system of FIG. 4 with the depth measurement separated from the surgical handpiece.

Referring to FIGS. 6-8, the handheld surgical instrument 402 comprises a controller 410 that is operably connected to the displacement sensor 422, through a set of housing connectors FIG. 8, 436 and instrument connectors 434. The controller 410 is configured to store in memory device 412 multiple signals related to the surgical procedure. As a non-limiting example, the controller 410 and the memory device 412 are located in a handheld surgical device. Alternatively, with reference to FIG. 4, the controller and/or memory device can be housed in a remote device 430, or possibly in the depth measurement module 416 itself.

It is contemplated that the controller 410 and the memory device 412 may communicate over a wired or a wireless connection. The wireless communications being facilitated by transceivers located on the controller and the memory device. These wireless communications transceivers would support protocols such as WI-FI, Bluetooth, or other similar wireless communications protocols. This surgical instrument may include a transceiver that sends data to a remote device 430, such as a tablet or external server, which may include a second transceiver.

Figure 1:
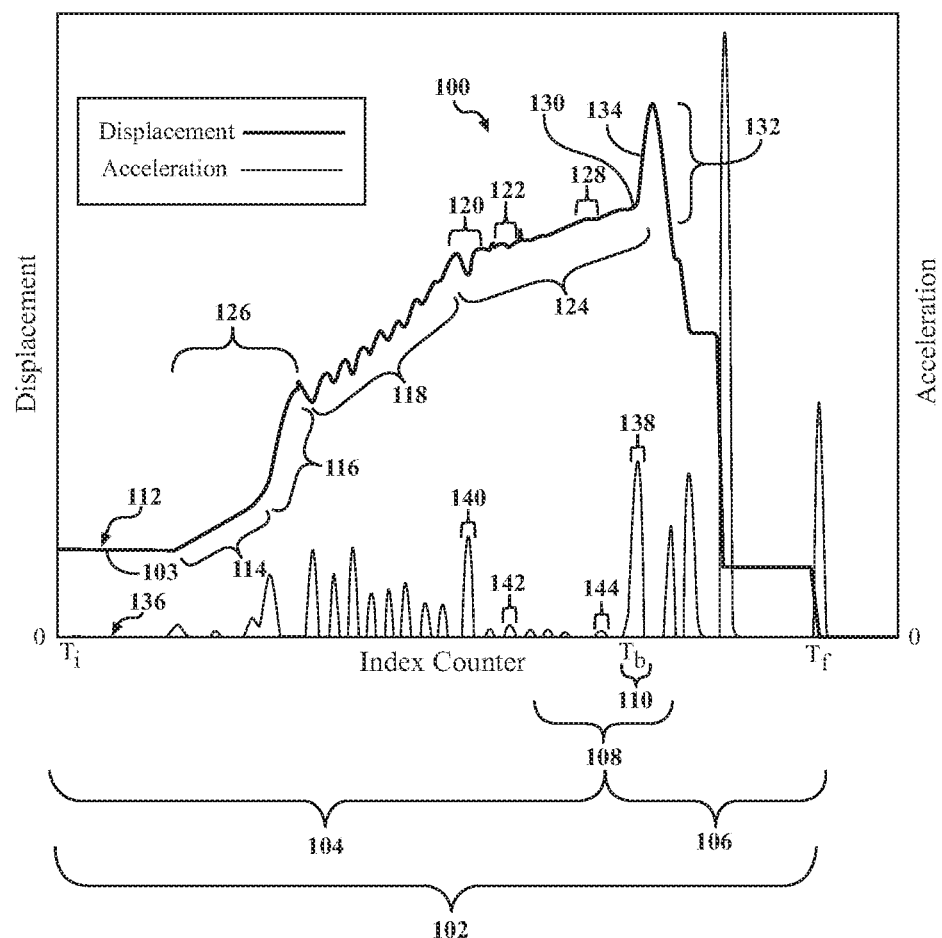
FIG. 1 is a graphical representation of the displacement signal and acceleration signal for a drilling process for a first type of bone.
Figure 2:
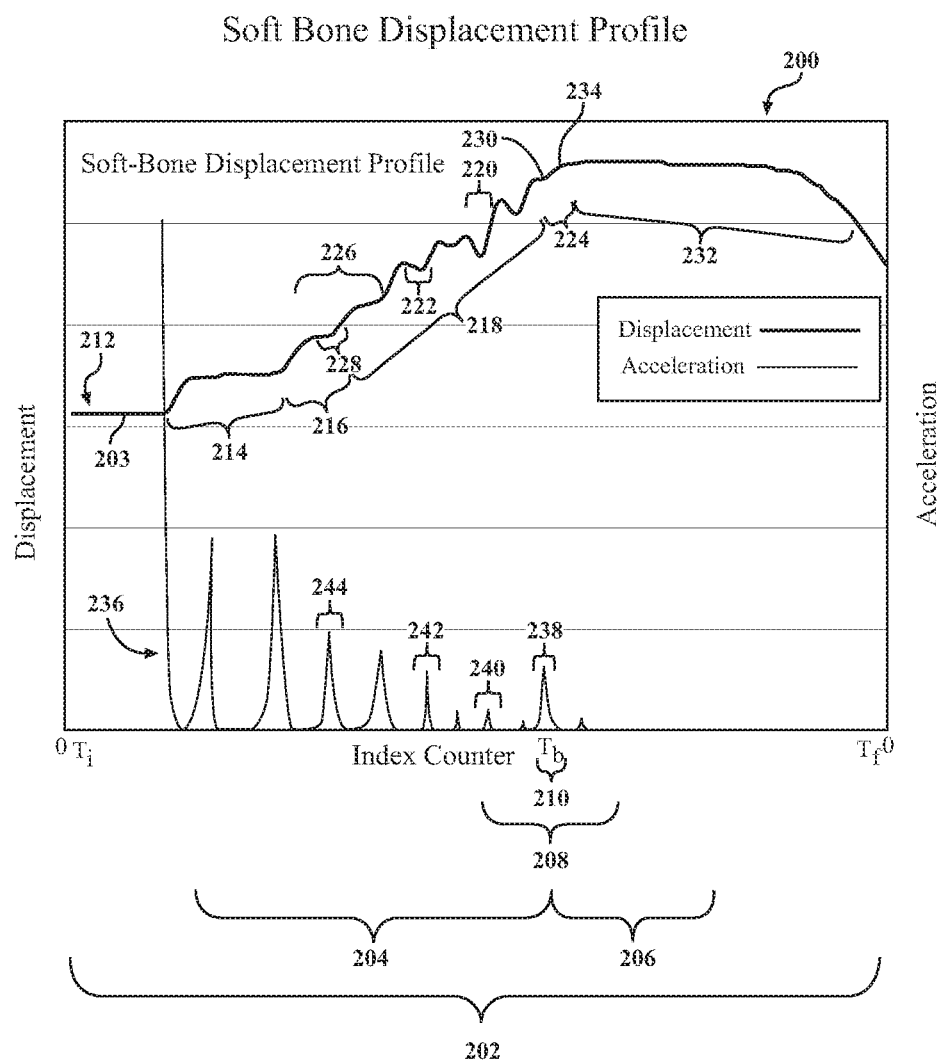
FIG. 2 is a graphical representation of the displacement signal and acceleration signal for a drilling process for a second type of bone.
Figure 3:
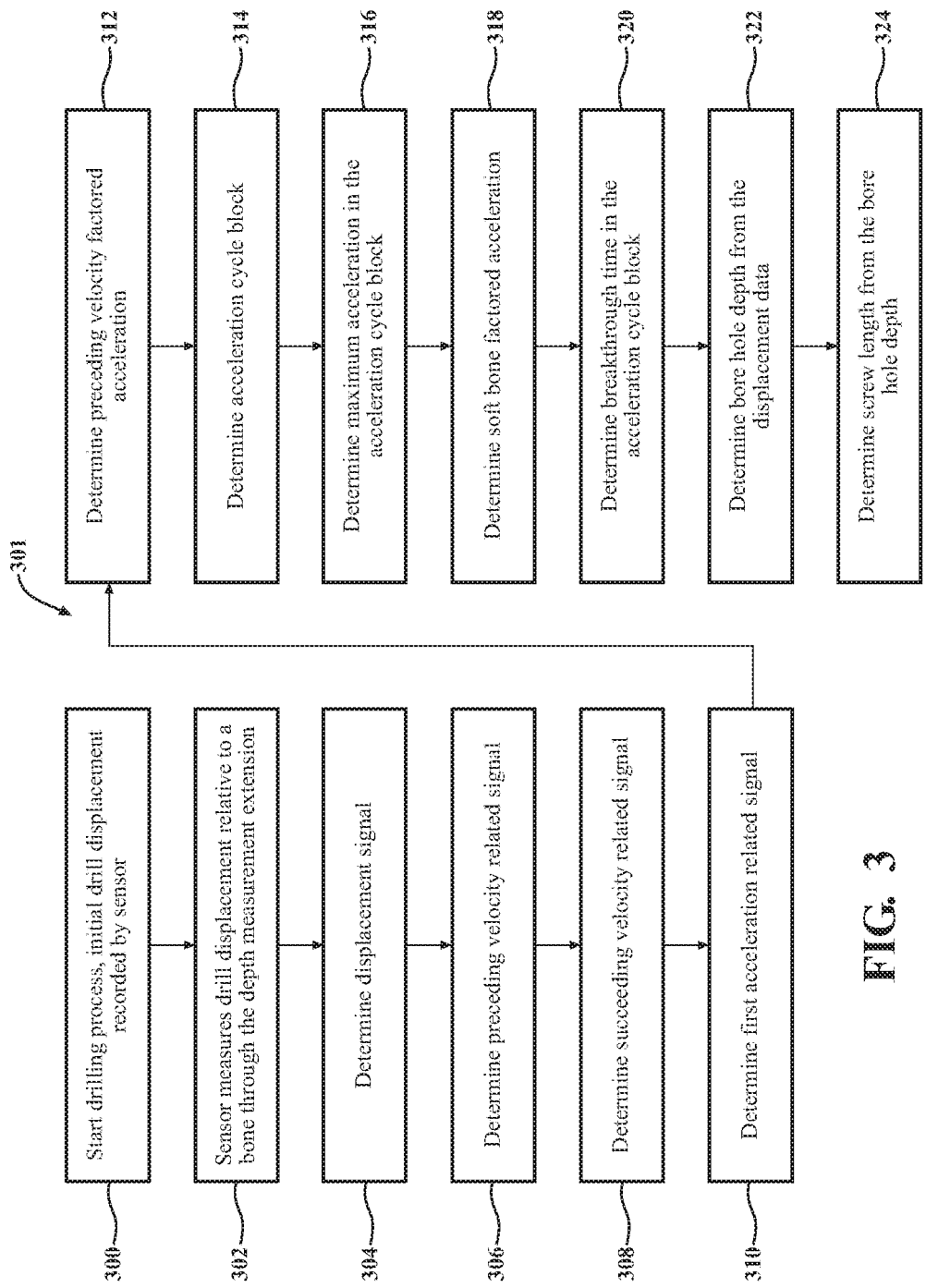
FIG. 3 illustrates the logical flow diagram of determining the proper screw length from the bore hole depth.

With reference to FIGS. 1-3, the displacement sensor 422 is operably connected to the depth measurement extension 420 such that the displacement sensor 422 is configured to provide a displacement signal 112, 212, 304 over a first time interval 102, 202 upon movement of the depth measurement extension 420. The first time interval 102, 202 is bounded by an initial time (Ti) and a final time (Tf), the first time interval 102, 202 corresponding to a drilling process. That is to say, (Ti) is when the surgeon places the drill in position to start a drilling procedure, and (Tf) is when the surgeon fully retracts the drill after performing the particular drilling of the bone such that the depth measurement extension 420 returns to its starting position.

Figure 10:
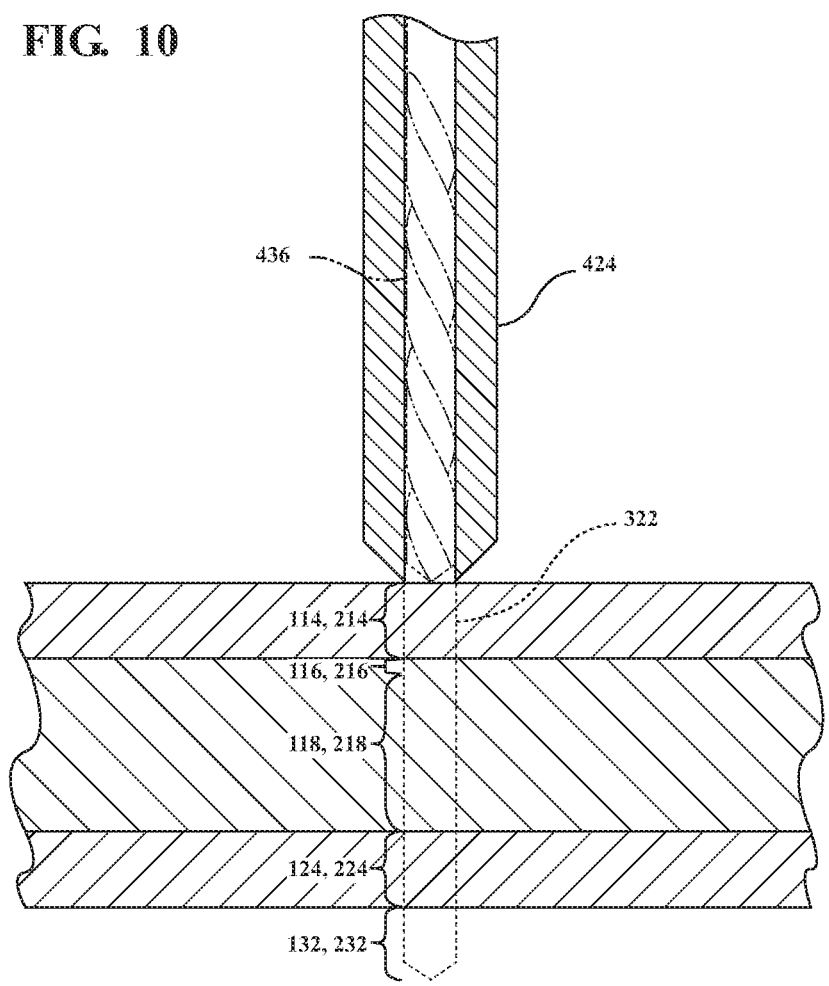
FIG. 10 is a cross sectional view of a bone abutted by a drill bit and measurement cannula from the system of FIG. 4 showing the movement of the drill bit through the bone, relative to the bone and relative to the depth measurement extension, and detailing the regions of the of the drilling process.
Figure 11:
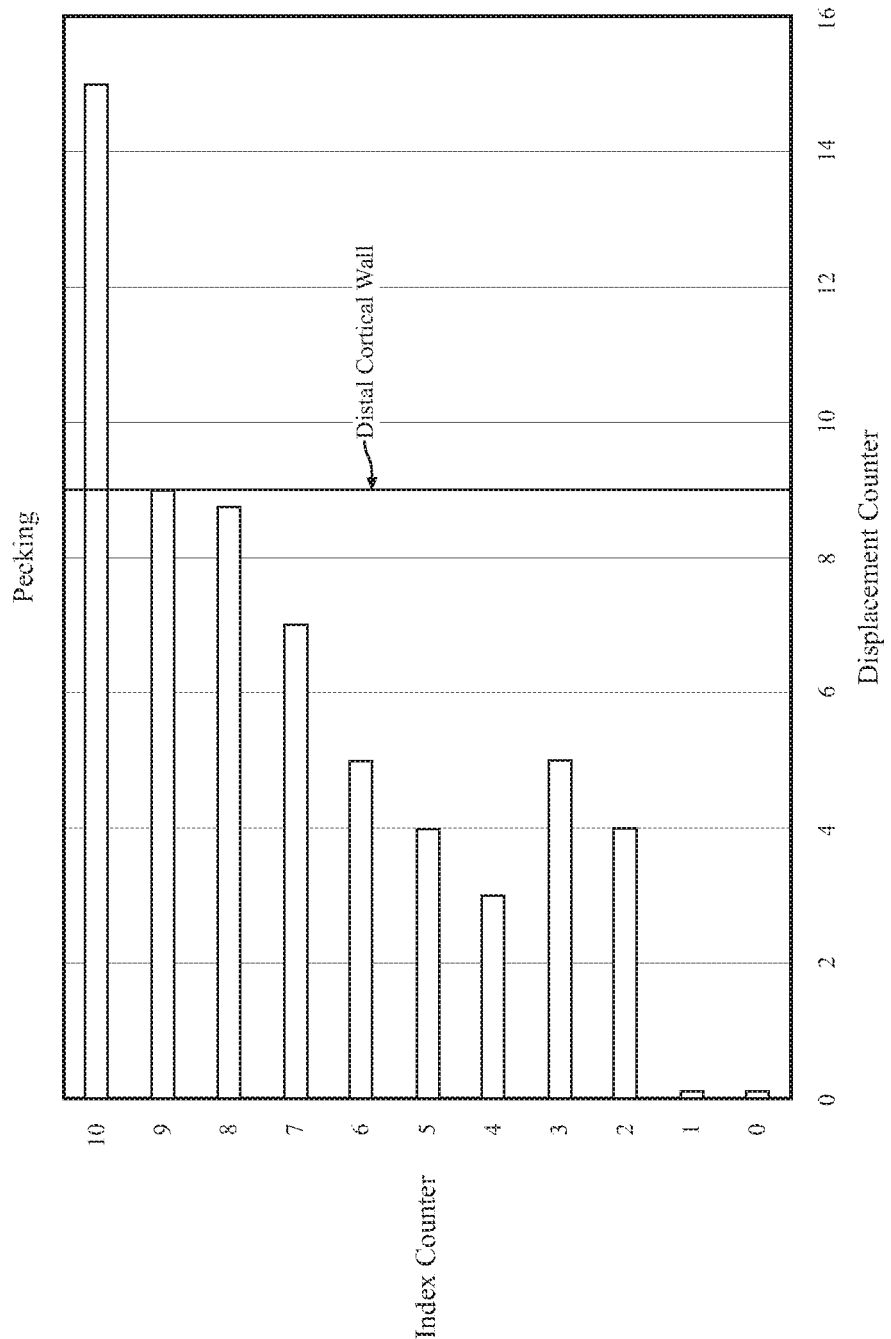
FIG. 11 is a quantized view of the displacement of the drill bit relative to a bone during a drilling procedure where a pecking event has occurred using fixed rate sampling.

Reference 100 in FIG. 1 shows the displacement and acceleration signal patterns typically seen in a drilling procedure for hard bone, hard bone being, for instance, a femur or a tibia, which has a significant cortical layer. This is compared to bones of the mid-foot, with a thin cortical layer or osteoporotic bones which are less resilient, which are considered soft bone. For ease of understanding, this displacement signal 112 is described in five distinct regions. Referring to FIGS. 1 and 11, the first region 114 is this portion of the curve corresponds to the surgeon drilling through the proximal cortex of the bone. The second region 116 is the breakthrough from the first cortex into the cancellous bone. Region three 118 is the drilling of the cancellous bone. The fourth region 124 is the surgeon drilling through the distal cortex with breakthrough displacement 130 followed by a plunge 134. Lastly, region five 132, is the breakthrough plunge from the second cortex followed by the retraction of the drill from the drilled bone. FIG. 10 shows the position of each of these regions relative to the bone.

FIG. 2 reference 200 reveals that unlike with hard bone, the drilling process for soft-bone lack the distinctiveness for the five distinct regions in the displacement signal. Referring to FIGS. 2 and 11, the first region 214 is this portion of the curve corresponds to the surgeon drilling through the proximal cortex of the bone, the signal, however, is less pronounced as with the hard bone above. The second region 216 is the breakthrough from the first cortex into the cancellous bone which is less distinctive than the signal for hard bone. Region three 218 is the drilling of the cancellous bone which is similar to the displacement signal for hard bone. The fourth region 224 is the surgeon drilling through the distal cortex with breakthrough displacement 230 followed by a plunge 234. Lastly, region five 232, is the breakthrough plunge from the second cortex followed by the retraction of the drill. As demonstrated by displacement signal 212, the breakthrough displacement 230 from the distal cortex is not well defined as there is minimal plunge 234 when compared to the hard bone above. This lack of definition along with inflections in the displacement signal 212 due to events like chip clearing, 222 by the drill bit, the pecking event 220, or trigger manipulation event 228 by the surgeon, determining the point of breakthrough displacement 230 becomes much more difficult—especially for soft-bone. Again, FIG. 10 shows the position of each of these regions relative to the bone.

As stated above, the inflections in the displacement signal have three primary causes: a chip clearing event 222, a pecking event 220, and a trigger manipulation event 228. These three phenomena are described with reference to FIGS. 1 and 2.

Referring to FIGS. 1 and 2, during a chip clearing event 122, 222, a bone chip or fragment is caught between the cutting face of the drill bit and the surface being cut. This chip causes a displacement proximally of the drill bit from the cut surface. The phenomena may be seen as a small backward movement in the displacement signal. When the chip is cleared and the bit moves forward, there is a small acceleration 142, 242 and a displacement increase back to the cut surface. The chip clearing event leads to extraneous data in the displacement signal 112, 212, and the first acceleration-related signal 136, 236 which can look like the drill bit breaking through the distal cortical wall, especially for soft-bone where there is a very small increase in the displacement slope corresponding to a breakthrough event.

A pecking event 120, 220 occurs when the surgeon pulls the surgical instrument back such that the drill bit retreats back from the cut surface a distance and then the surgeon pushes the drill forward to contact the cut surface. A pecking event 120, 220 in turn cause the hand piece to move backward and forward in relationship to the depth measurement extension 420. Like the chip clearing event 122, 222, the pecking event 120, 220 causes confounding artifacts to appear in the displacement signal 112, 212 and the first acceleration-related signal 136, 236. These extraneous data lead to inflections in the first acceleration-related signal 136,236 which can mimic the breakthrough displacement 130, 230 or mask the actual breakthrough displacement 130, 230. The inflection in the first acceleration-related signal 136, 236 due to pecking 140, 240 can be larger than in the case of the chip clearing event 122, 222 and may lead to more prominent disturbances in both the displacement signal 112, 212 and the first acceleration-related signal 136, 236.

Lastly, trigger manipulation event 128, 228 may cause inflections in the displacement signal 112, 212 and acceleration-related signals 136, 236. However, unlike chip clearing or pecking, trigger manipulation does not cause the drill bit to retreat from the cut surface. During trigger manipulation event 128, 228 there is no reversal in the displacement signal 112, 212. Nonetheless, there is an inflection related to the trigger manipulation 144, 244. These perturbations in the displacement signal 112, 212 and the first acceleration-related signal 136, 236 may be mitigated by an algorithm implemented the controller 410 (FIGS. 4 and 6) as described below.

The controller 410 implements a breakthrough algorithm on the displacement signal 112, 212, 304 to determine the bore hole depth FIG. 3 322, and from that, optionally, the screw length. The algorithm may be implemented as one or more software components, through subroutines, or logic and one or more hardware components (e.g., processor, ASIC, register, FPGA, circuit, logic circuit, and the like) or a combination of hardware and software components comprising the controller. In one example, the logic that executes the breakthrough algorithm as depicted in flow chart in FIG. 3, 301 is stored in a memory device. The memory device may be located in the hand piece, the FIG. 6, 412 or the memory device may reside in a remote device FIG. 4, 412. The algorithm could be built into an ASIC or FPGA or other similar component or circuit.

The breakthrough algorithm is briefly summarized by the flow chart FIG. 3, 301, and will be described here, used with a rotary cutting tool, as an example. This example is not a limitation as other configurations are contemplated, such as a burr or a reamer. For clarity of disclosure, six examples of the application of the algorithm are described.

Example 1

Acceleration Cycle Blocks and Soft-Bone Factored Acceleration

Referring to FIGS. 1-3, 6 and 7 at the start of the drilling process 300, the displacement sensor 422 measures an initial displacement 103, 203, 302 which the controller 410 writes to the memory device 412. The controller 410 is configured to determine a preceding velocity-related signal 306 from the displacement signal 112, 212, 304 over a second time interval 104, 204, where the second time interval is at least a portion of the first time interval 102, 202. The controller 410 then determines a succeeding velocity-related signal 308 over a third time interval 106, 206 based on the displacement signal 112, 212, 304 where the third time interval 106, 206 is within the first time interval 102, 202, and the second time interval 104, 204 precedes the third time interval 106, 206. Furthermore, where the displacement at a time within the first time interval 102, 202 of the displacement signal 112, 212, 304 is greater than a previous maximum displacement within the first time interval 102, 202, that is, displacement $X_{t+1} > X_t$, the controller 410 ascertains a first acceleration-related signal 310 within a fourth time interval 108, 208. Stated another way, only for forward drilling time interval 126, 226, where the displacement of the drill is greater than the last maximum displacement, within the fourth time interval 108, 208 is the first acceleration-related signal 136, 236, 310 calculated. The fourth time interval 108, 208 includes at least a portion of the second time interval 104, 204, and at least a portion of the third time interval 106, 206. The controller 410 also determines a preceding velocity factored acceleration-related signal 312 for the fourth time interval 108, 208 derived from the first acceleration-related signal 136, 236, 310 and the preceding velocity-related signal 306. The aforementioned steps remove the noise from the first acceleration-related signal 136, 236, 310 and preceding velocity factored acceleration-related signal 312 due to the chip clearing event 122, 222, the trigger manipulation event 128, 228, and/or pecking event 120, 220.

The controller 410 then identifies an acceleration cycle block 138, 238, 314 within a portion of the first acceleration-related signal 136, 236, 310, the acceleration cycle block 138, 238, 314 corresponding to a fifth time interval 110, 210, where increasing acceleration related signal values precede decreasing acceleration related signal values during a forward drilling time interval 126, 226. The acceleration cycle block 138,238, 314 may be identified with a breakthrough displacement 130, 230 and plunge 134, 234. The controller 410 determines the maximum acceleration within the acceleration cycle block 138, 238, 314 inside the fifth time interval 110, 210. A soft-bone factored acceleration 318 is determined by the controller 410 for the fifth time interval 110, 210 based on the preceding velocity factored acceleration-related signal 312 and the succeeding velocity-related signal 308 at maximum acceleration. The controller 410 then proceeds to determine a maximum soft-bone factored acceleration 318 within the fourth time interval 108, 208. A breakthrough time 320 of the drill bit through a distal cortical wall of the bone within the first time interval 102, 202 as the time corresponding to the maximum soft-bone factored acceleration is determined by the controller 410. From the breakthrough displacement 130, 230 at breakthrough time (Tb) and the initial displacement 103, 203, 302 the bore hole depth FIG. 10, 322 is determined by the controller 410. A screw length 324 is then determined from the bore hole depth 322 by the controller 410 and sent to the display 428.

In determining the screw length other information may be used along with the bore hole depth 322. An example is the thickness of an orthopedic plate to be installed. Another example is the manufacture's information relating to optimal screw lengths for specific orthopedic kits. And perhaps, the characteristics of the bone being repaired would be a further example.

Example 2

Acceleration Cycle Block

Example 2 includes finding the screw length via bore hole depth using an acceleration cycle block to determine breakthrough of the bit from the distal cortical wall. As above, referring to FIGS. 1-3, 6 and 7 at the start of the drilling process 300 the displacement sensor 422 measures an initial displacement 103, 203, 302 which the controller 410 writes to the memory device 412. For at least one forward drilling time interval 126, 226, where the displacement at a time within the first time interval 102, 202 of the displacement signal 112, 212, 304 is greater than a previous maximum displacement within the first time interval 102, 202, that is, displacement $X_{t+1} > X_t$, the controller 410 ascertains a first acceleration-related signal 136, 236, 310 within a second time interval 104, 204. The second time interval 104, 204 includes at least a portion of the first time interval 102, 202. The controller 410 then identifies an acceleration cycle block 138, 238, 314 within a portion of the first acceleration-related signal 136, 236, 310. The controller 410 determines the maximum acceleration within the acceleration cycle block 138, 238, 314, as described in Example 1. A breakthrough time (Tb) of the drill bit through a distal cortical wall of the bone is determined by the controller, 410 within the acceleration cycle block 138, 238, 314. The breakthrough time (Tb) is defined as determined point of maximum acceleration within the acceleration cycle block. From the breakthrough displacement 130, 230 at breakthrough time (Tb) and the initial displacement 103, 203, 302 from the displacement signal 112, 212, 304, the bore hole depth FIG. 10. 322 is determined by the controller 410. A screw length 324 is then determined from the bore hole depth by the controller 410 and sent to the display 428 for indication to the user.

Example 3

Preceding Velocity-Factored Acceleration

In Example 3, the screw length is determined from bore hole depth by employing the preceding velocity-factored acceleration to identify breakthrough of the bit from the distal cortical wall. As in the preceding example, referring to FIGS. 1-3, 6 and 7, at the start of the drilling process 300, the displacement sensor 422 measures an initial displacement 103, 203, 302 which the controller 410 writes to the memory device 412. The controller 410 is configured to determine a preceding velocity-related signal 306 from the displacement signal 112, 212, 304 over a second time interval 104, 204, where the second time-interval is at least a portion of the first time interval 102, 202.

Here, however, is where Example 3 diverges from Example 2. The controller 410 determines a first acceleration-related signal 136, 236, 310 over a third time interval 106, 206 based on the displacement signal 112, 212, 304 where the third time interval 106, 206 is within the first time interval 102, 202, and the second time interval 104, 204 precedes the third time interval 106, 206. The controller 410 next determines a preceding velocity factored acceleration-related signal 312 for the third time interval 106, 206 based on the first acceleration-related signal 136, 236, 310 and the preceding velocity-related signal 306. For example, preceding velocity at point in time (n) may be calculated based on one or more of the following equations (EQs):

Preceding Velocity(n)=Displacement(n)−Displacement(n−x)  EQ 1:

Succeeding Velocity(n)=Displacement(n+x)−Displacement(n)  EQ 2:

Acceleration(n)=Succeeding Velocity(n)−Preceding Velocity(n)  EQ 3:

Preceding Velocity Factored Acceleration(n)=Acceleration(n)/Preceding Velocity(n)  EQ 4:

where D(n) is displacement at point in time n and D(n-x) is prior displacement to point in time n, and D(n+x) is advance displacement to point in time n.

The breakthrough time (Tb) of the drill through the distal cortical wall of the bone within the first time interval 102, 202 based on the preceding velocity factored acceleration-related signal 312. The bore hole depth 322 is determined from the initial displacement 103, 203, 302 of the displacement signal 112, 212, 304 and the breakthrough displacement 130, 230 from the displacement signal 112, 212, 304 at the breakthrough time (Tb). The controller 410 determines a screw length 324 and based on the bore hole. The controller 410 displays the screw length indicator on the display 428 to which the controller 410 is connected.

Example 4

Soft-Bone

In Example 4, the screw length is computed from bore hole depth by using the soft-bone factored acceleration to identify breakthrough of the bit from the distal cortical wall. Like the previous two examples, referring to FIGS. 1-3, 6 and 7, at the start of the drilling process 300, the displacement sensor 422 measures an initial displacement 103, 203, 302 to which controller 410 writes to the memory device 412. The controller 410 is configured to determine a preceding velocity-related signal 306 from the displacement signal 112, 212, 304 over a second time interval 104, 204, where the second time interval is at least a portion of the first time interval 102, 202. The controller determines a preceding velocity-related signal 306 over a second time interval 104, 204, where the second time interval is at least a portion of the first time interval 102, 202. The controller 410 ascertains a succeeding velocity-related signal 308 over a third time interval 106, 206 where the third time interval 106, 206 falls within the first time interval 102, 202 and is preceded by the second time interval 104, 204. A first acceleration-related signal 136, 236, 310 is derived by the controller over a fourth time interval 108, 208, where the fourth time interval is at least a portion of the second time interval 104, 204 and at least a portion of the third time interval 106, 206. The controller determines a preceding velocity factored acceleration-related signal 312 over the fourth time interval 108, 208 based on the preceding velocity-related signal 306 and the first acceleration-related signal 136, 236, 310. For example, the controller may use EQs 1-4 described in the preceding example to determine the preceding velocity factored acceleration-related signal 312 over the fourth time interval 108, 208.

Next, the controller 410 calculates the soft-bone factored acceleration 318 over the fourth time interval 108, 208 based on the preceding velocity-related signal 308 over the third time interval 106, 206. The controller 410 derives a breakthrough time (Tb) of the drill bit through a distal cortical wall of the bone within the first time interval 102, 202 based on the maximum soft-bone factored acceleration 318. A bore hole depth 322 is ascertained from an initial displacement 103, 203, 302 from the displacement signal 112, 212 304 and a breakthrough displacement 130, 230 from the displacement signal 112, 212, 304 at the breakthrough time (Tb). A display 428 may be configured to receive the output of a screw length 324 indicator based on the bore hole depth 322 from the controller 410.

Example 5

Remote Controller/Display

Referring to FIGS. 1-3, 6 and 7, the example 5 case as in case 2 includes finding the screw length via bore hole depth using an acceleration cycle block to determine breakthrough of the bit from the distal cortical wall. The acceleration cycle block as defined in Example 1 may be associate a period of breakthrough displacement 130, 230 and plunge 134, 234. In example 5, the controller, the memory device, the display, or a combination there of can be placed in a remote device 430. The handheld surgical instrument 402 is connected to the remote device 430 via a wired or wireless connection. This example contemplates that the remote device 430 remote device is a mobile device 432 such as a tablet, a smartphone, or a laptop. However, the remote device 430 can be a workstation or a desktop computer.

Referring to FIGS. 6-8, at the start of the drilling process 300, the displacement sensor 422 measures an initial displacement 103, 203, 302 which the controller 410 writes to the memory device 412. For at least one forward drilling time interval 126, 226, where the displacement at a time within the first time interval 102, 202 of the displacement signal 112, 212, 304 is greater than a previous maximum displacement within the first time interval 102, 202, that is, displacement $X_{t+1} > X_t$, the controller 410 ascertains a first acceleration-related signal 310 within a second time interval 104, 204. The second time interval 104, 204 includes at least a portion of the first time interval 102, 202. The controller 410 then identifies an acceleration cycle block 138, 238, 314 within a portion of the first acceleration-related signal 136, 236, 310. The controller, 410 determines the maximum acceleration within the acceleration cycle block 316. A breakthrough time (Tb) of the drill bit through a distal cortical wall of the bone is determined by the controller, 410 within the acceleration cycle block 138, 238, 314. The breakthrough time (Tb) is defined as determined point of maximum acceleration within the acceleration cycle block. From the displacement at breakthrough time (Tb) and the starting displacement from the displacement signal 112, 212, 304, the bore hole depth FIG. 10, 322 is determined by the controller 410. A screw length 324 is then determine from the bore hole depth by the controller 410 and sent to the display 428.

In this example, the displacement sensor 422 that is mounted in the handheld surgical instrument 402 is in communication with the controller 410 located in the remote device 430 over the wired or wireless connection. The controller 410 is functionally connected the memory device 412 which may also be located in the remote device 430. As part of the surgical procedure, the controller 410 writes to the memory device 412 at least a portion of the displacement signal 112, 212, 304. For at least one forward drilling time interval 126, 226, where the displacement at a time within the first time interval 102, 202 of the displacement signal 112, 212, 304 is greater than a previous maximum displacement within the first time interval 102, 202, that is, displacement $X_{t+1} > X_t$, the controller 410 writes at least a portion of the first acceleration-related signal 136, 236, 310 to the memory device 412. At the end of the procedure the controller 410 located in the remote device 430 transmits a screw length 324 to the display 428 also located with the remote device 430, to which the controller is functionally connected.

Example 6

Tool in General

Example 6 case describes a handheld surgical instrument that determine the bore-depth of the hole created during the surgical process. Following the steps in Example 1, and referring to FIGS. 1-3, 6 and 7, at the start of the drilling process 300, the displacement sensor 422 measures an initial displacement 103, 203, 302 which controller 410 writes to the memory device 412. The controller 410 is configured to determine a preceding velocity-related signal 306 from the displacement signal 112, 212, 304 over a second time interval 104, 204, where the second time interval is at least a portion of the first time interval 102, 202. The controller 410 then determines a succeeding velocity-related signal 308 over a third time interval 106, 206 based on the displacement signal 112, 212, 304, where the third time interval 106, 206 is within the first time interval 102, 202, and the second time interval 104, 204 precedes the third time interval 106, 206. Furthermore, where the displacement at a time within the first time interval 102, 202 of the displacement signal 112, 212, 304 is greater than a previous maximum displacement within the first time interval 102, 202, that is, displacement $X_{t+1} > X_t$, the controller 410 ascertains a first acceleration-related signal 136, 236, 310 within a fourth time interval 108, 208. Stated another way, only for forward drilling time interval 126, 226 within the fourth time interval 108, 208 is the first acceleration-related signal 136, 236, 310 calculated. The fourth time interval 108, 208 includes at least a portion of the second time interval 104, 204, and at least a portion of the third time interval 106, 206. The controller 410 also determines a preceding velocity factored acceleration-related signal 312 for the fourth time interval 108, 208 derived from the first acceleration-related signal 136, 236, 310 and the preceding velocity-related signal 306. The preceding steps remove the noise from the first acceleration-related signals 136, 236, 310, and the preceding velocity factored acceleration-related signal 312 due to the chip clearing event 122, 222, the trigger manipulation event 128, 228, and pecking event 120, 220.

The controller 410 then identifies an acceleration cycle block 138, 238, 314 within a portion of the first acceleration-related signal 136, 236, 310 the acceleration cycle block 138, 238, 314 corresponding to a fifth time interval 110, 210, where increasing acceleration related signal values precede decreasing acceleration related signal values. The controller 410 determines the maximum acceleration within the acceleration cycle block 138, 238, 314 inside the fifth time interval 110, 210. A soft-bone factored acceleration 318 is determined by the controller 410 for the fifth time interval 110, 210 based on the preceding velocity factored acceleration-related signal 312 and the succeeding velocity-related signal 308 at maximum acceleration. The controller 410 then proceeds to determine a maximum soft-bone factored acceleration 318 within the fourth time interval 108, 208. A breakthrough time 320 of the drill bit through a distal cortical wall of the bone within the first time interval 102, 202 as the time corresponding to the maximum soft-bone factored acceleration is determined by the controller, 410. From the breakthrough displacement 130, 230 at breakthrough time (Tb) and the initial displacement 103, 203, 302 the bore hole depth FIG. 10 322 is determined by the controller 410. The controller 410 sends to the display 436 the bore hole depth 322.

Referring to FIGS. 1-3, the previously mentioned signal are based on a system-clock signal which, in non-limiting examples of a system clock-signals are, the internal clock signal of the processor, or a clock-signal from separate clock device. The system clock-signal is used to define the sample rate at which the displacement measurements are taken and indexed over the first time interval 102, 202 creating displacement signal 112, 212, 304. It is contemplated the sample rate may be fixed, or alternatively, the sample rate may be variable, or procedure dependent. FIG. 11 shows a quantized view of a drilling procedure with a pecking event as an example of fixed rate sampling. The controller 410 receives a displacement signal 112, 212, 304 from the displacement sensor 422 and writes the displacement signal 112, 212, 304, to a memory device 412 to which the controller is operably connected. The controller also writes to the memory device other signals, including, but are not limited to, displacement, velocity-related signals, acceleration-related signals, preceding velocity-factored acceleration related signal, and soft-bone factored acceleration signal.

Furthermore, the acceleration-related signal can be derived from the displacement signal or, alternatively, the acceleration-related signal can be provided by another sensor, for instance an accelerometer which is coupled to the depth measurement extension 420 and provides a signal to the controller 410.

Clause 1—A handheld surgical instrument system configured to determine a suitable screw length for bone fixation during a process of drilling bone, said instrument system comprising: a housing; a motor (414) positioned within said housing (406); a depth measurement extension (420) movably coupled to said housing (406); a displacement sensor (422) operably connected to said depth measurement extension (420) such that said displacement sensor (422) is configured to provide a displacement signal (112, 212, 304) over a first time interval (102, 202) upon movement of said depth measurement extension (420), said first time interval (102, 202) being bounded by an initial time (Ti) and a final time (Tf), said first time interval (102, 202) corresponding to a drilling process; a controller (410) operably connected to said displacement sensor (422) to receive said displacement signal (112, 212, 304); a memory device (412) operably connected to a controller (410), where said memory device (412) is configured to store data; wherein said controller (410) is configured to: determine a preceding velocity-related signal (306) from said displacement signal (112, 212, 304) over a second time interval (104, 204), where said second time interval (104, 204) is at least a portion of said first time interval (102, 202); determine a succeeding velocity-related signal (308) over a third time interval (106, 206) based on said displacement signal (112, 212, 304), said third time interval (106, 206) being within said first time interval (102, 202), said second time interval (104, 204) preceding said third time interval (106, 206); determine at least one forward drilling time interval (126, 226) within said first time interval (102, 202), where said displacement signal (112, 212, 304) is greater than a previous maximum displacement within said first time interval (102, 202); determine a first acceleration-related signal (136, 236, 310) within a fourth time interval (108, 208), said fourth time interval (108, 208) including at least a portion of said second time interval (104, 204) and said third time interval (106, 206) based on said displacement signal (112, 212, 304), wherein said fourth time interval (108, 208) includes only the at least one forwarding drilling time interval (126, 226); determine a preceding velocity factored acceleration-related signal (312) for said fourth time interval (108, 208) based on said first acceleration-related signal (136, 236, 310) and said preceding velocity-related signal (306); identify an acceleration cycle block (138, 238, 314) within said portion of first acceleration-related signal (136, 236, 310), said acceleration cycle block (138, 238, 314) corresponding to a fifth time interval (110, 210) where increasing acceleration-related signal values precede decreasing acceleration related signal values; determine a maximum acceleration in the acceleration cycle block (316) within the fifth time interval (110, 210); determine a soft-bone factored acceleration (318) for said fifth time interval (110, 210) based on said preceding velocity factored acceleration-related signal (312) and said succeeding velocity-related signal (308) at maximum acceleration; determine a maximum soft-bone factored acceleration (318) within said fourth time interval (108, 208); determine a breakthrough time (Tb) of the drill bit through a distal cortical wall of the bone within said first time interval (102, 202) as the time corresponding to the maximum soft-bone factored acceleration (318); determine a depth of the bore hole (322) from a starting displacement from said displacement signal (112, 212, 304) and a breakthrough displacement (130, 230) from said displacement signal (112, 212, 304) at said breakthrough time (Tb); and determine a screw length (324) based on the depth of the bore hole (322); a display (428) operably connected to said controller (410) displaying output of a screw length indicator based on said bore hole (322) depth.

Clause 2—A handheld surgical instrument as recited in clause 1, wherein said controller (410) writes to said memory device (412) at least a portion of said preceding velocity factored acceleration-related signal (312).

Clause 3—A handheld surgical instrument as recited in clause 1, wherein said controller (410) writes to said memory device (412) at least a portion of said soft-bone factored acceleration signal (318).

Clause 4—A handheld surgical instrument as recited in clause 1, wherein said depth measurement extension (420) is a cannula.

Cause 5—A handheld surgical instrument configured to determine a suitable screw length for bone fixation during a process of drilling bone, said instrument comprising: a displacement sensor (422) configured to provide a displacement signal (112, 212, 304) over a first time interval (102, 202), said first time interval (102, 202) being bounded by an initial time (Ti) and a final time (Tf), said first time interval (102, 202) corresponding to a drilling process; a controller (410) operably connected to said displacement sensor (422) to receive said displacement signal (112, 212, 304); a memory device (412) operably connected to a controller (410), where said memory device (412) is configured to store data; wherein said controller (410) is configured to: determine at least one forward drilling time interval (126, 226) within said first time interval (102, 202), where said displacement signal (112, 212, 304) is greater than a previous maximum displacement within said first time interval (102, 202); determine a first acceleration-related signal (136, 236, 310) from said displacement signal (112, 212, 304) over a second time interval (108, 208), where said second time interval (108, 208) is at least a portion of said first time interval (102, 202); identify an acceleration cycle block (138, 238, 314) within said portion of said first acceleration-related signal (136, 236, 310), said acceleration cycle block (138, 238, 314) corresponding to a third time interval (110, 210) where increasing acceleration related signal values precede decreasing acceleration related signal values, wherein said third time interval (110, 210) is at least a portion of said first time interval (102, 202); determine a maximum acceleration in the acceleration cycle block (316);

determine a breakthrough time (Tb) of the drill bit through a distal cortical wall of the bone within said acceleration cycle block (138, 238, 314); and determine a depth of the bore hole (322) from a starting displacement from said displacement signal (112, 212, 304) and a breakthrough displacement (130, 230) from said displacement signal (112, 212, 304) at said breakthrough time (Tb); determine a screw length (324) based on the depth of the bore hole (322) at said breakthrough time (Tb).

Clause 6—A handheld surgical instrument as recited in clause 5, wherein the step of determining a breakthrough time (Tb) is further defined as determining a maximum acceleration within the acceleration cycle block (138, 238, 314).

Clause 7—A handheld surgical instrument as recited in clause 5, wherein said handheld surgical instrument comprises a housing (406).

Clause 8—A handheld surgical instrument as recited in clause 5, wherein said handheld surgical instrument comprises a motor (414) positioned within said housing (406).

Clause 9—A handheld surgical instrument as recited in clause 5, wherein said handheld surgical instrument comprises a depth measurement extension (420), where said depth measurement extension (420) is operably coupled to said housing (406).

Clause 10—A handheld surgical instrument as recited in clause 5, wherein said displacement sensor (422) is a potentiometer.

Clause 11—A handheld surgical instrument as recited in clause 5, wherein said displacement sensor (422) is operationally coupled to said depth measurement extension (420) to provide said displacement signal (112, 212, 304) based on a position of said depth measurement extension (420).

Clause 12—A handheld surgical instrument as recited in clause 5, wherein said depth measurement extension (420) is a cannula.

Clause 13—A handheld surgical instrument as recited in clause 5, further comprising a display (428), said display (428) configured to output a screw length indicator based on said bore hole depth.

Clause 14—A handheld surgical instrument as recited in clause 5, wherein said controller (410) writes to said memory device (412) at least a portion of said displacement signal (112, 212 304).

Clause 15—A handheld surgical instrument as recited in clause 5, wherein said controller (410) writes to said memory device (412) at least a portion of said first acceleration-related signal (136, 236, 310) for said at least one forward drilling time intervals (126, 226) within said first displacement signal (112, 212 304) within said first time interval (102, 202).

Clause 16—A system configured to a determine a suitable screw length for bone fixation during a process of drilling bone with a drill bit, said system comprising: a handheld surgical instrument (402) comprising a displacement sensor (422) configured to provide a displacement signal (112, 212, 304) over a first time interval (102, 202), said first time interval (102, 202) being bounded by an initial time (Ti) and a final time (Tf), said first time interval (102, 202) corresponding to a drilling process; a controller (410) operably connected to said displacement sensor (422) to receive said displacement signal (112, 212, 304); a memory device (412) operably connected to a controller (410), where said memory device (412) is configured to store data; wherein said controller (410) is configured to: determine at least one forward drilling time interval (126, 226) within said first time interval (102, 202), where said displacement signal (112, 212, 304) is greater than a previous maximum displacement within said first time interval (102, 202); determine a first acceleration-related signal (136, 236, 310) from said displacement signal (112, 212, 304) over a second time interval (108, 208), where said second time interval (108, 208) is at least a portion of said first time interval (102, 202); identify an acceleration cycle block (138, 238, 314) within said portion of said first acceleration-related (136, 236, 310), said acceleration cycle block (138, 238, 314) corresponding to a third time interval (110, 210) where increasing acceleration related signal values precede decreasing acceleration related signal values, wherein said third time interval (110, 210) is at least a portion of said first time interval (102, 202); determine a maximum acceleration in the acceleration cycle block (316); determine a breakthrough time (Tb) of the drill bit through a distal cortical wall of the bone within said acceleration cycle block (138, 238, 314); and determine a depth of the bore hole (322) from a starting displacement from said displacement signal (112, 212, 304) and a breakthrough displacement (130, 230) from said displacement signal (112, 212, 304) at said breakthrough time (Tb); determine a screw length (324) based on the depth of the bore hole (322) at said breakthrough time (Tb).

Clause 17—A system as recited in clause 16, wherein the step of determining a breakthrough time (Tb) is further defined as determining a maximum acceleration within the acceleration block (138, 238, 314).

Clause 18—A system as recited in clause 16, wherein said system comprises a housing (406).

Clause 19—A system as recited in clause 16, wherein said system comprises a motor (414) positioned within said housing (406).

Clause 20—A system as recited in clause 16, wherein said system comprises a depth measurement extension (420), where said depth measurement extension (420) is operably coupled to said housing 406).

Clause 21—A system as recited in clause 16, wherein said displacement sensor (422) is a potentiometer.

Clause 22—A system as recited in clause 16, wherein said displacement sensor (422) is operationally coupled to said depth measurement extension (420) to provide said displacement signal (112, 212, 304) based on a position of said depth measurement extension (420).

Clause 23—A system as recited in clause 16, wherein said depth measurement extension (420) is a cannula.

Clause 24—A system as recited in clause 16, wherein said controller (410) writes to said memory device (412) at least a portion of said displacement signal (112, 212, 304).

Clause 25—A system as recited in clause 16, wherein said controller (410) writes to said memory device (412) at least a portion of said first acceleration-related signal (136, 236, 310) for said at least one forward drilling time interval (126, 226), where said displacement signal (112, 212, 304) is greater than a previous maximum displacement within said first time interval (102, 202).

Clause 26—A system as recited in clause 16, further comprising a display (428), said display (428) configured to output a screw length indicator based on said bore hole (322) depth.

Clause 27—A system as recited in clause 16, further comprising a remote device (430) in communication with said displacement sensor (422) of said handheld surgical instrument (402), said remote device (430) comprising said controller (410).

Clause 28—A system as recited in clause 16, further comprising a remote device (430) in communication with said displacement sensor (422) of said handheld surgical instrument (62), said remote device (430) comprising said memory device (412).

Clause 29—A system as recited in clause 27 or 28, wherein said remote device (430) is a mobile device (432).

Clause 30—A system as recited in clause 27 or 28, wherein said remote device (430) comprises a display (428), said display (428) configured to output a screw length indicator based on said bore hole (322) depth.

Clause 31—A handheld surgical instrument configured to determine bone thickness comprising: a displacement sensor configured (422) to provide a displacement signal (112, 212, 304) over a first time interval (102, 202), said first time interval (102, 202) being bounded by an initial time (Ti) and a final time (Tf), said first time interval (102, 202) corresponding to a drilling process; a controller (410) operably connected to said displacement sensor (422) to receive said displacement signal (112, 212, 304); a memory device (412) operably connected to said controller (410), where said memory device (412) is configured to store data; wherein said controller (410) is configured to: determine a preceding velocity-related signal (306) from said displacement signal (112, 212, 304) over a second time interval (104, 204), where said second time interval (104, 204) is at least a portion of said first time interval (102, 202); determine a first acceleration-related signal (136, 236, 310) over a third time interval (108, 208) based on said displacement signal (112, 212, 304), said third time interval (108, 208) being within said first time interval (102, 202), where said third time interval (108, 208) is after said second time interval (104, 204); determine a preceding velocity factored acceleration-related signal (312) for said third time interval (108, 208) based on said first acceleration-related signal (136, 236, 310) and said preceding velocity-related signal (306); determine a breakthrough time (Tb) of the drill bit through a distal cortical wall of the bone within said first time interval based on said preceding velocity factored acceleration-related signal (312); and determine a depth of the bore hole (322) from a starting displacement from said displacement signal (112, 212, 304) and a breakthrough displacement (130, 230) from said displacement signal (112, 212, 304) at said breakthrough time (Tb); determine a screw length (324) based on the depth of the bore hole (322); a display (428) operably connected to said controller (410) displaying output of a screw length indicator.

Clause 32—A handheld surgical instrument as recited in clause 31, wherein said handheld surgical instrument comprises a housing (406).

Clause 33—A handheld surgical instrument as recited in clause 31, wherein said handheld surgical instrument comprises a motor (414) positioned within said housing (406).

Clause 34—A handheld surgical instrument as recited in clause 31, wherein said handheld surgical instrument comprises a depth measurement extension (420), where said depth measurement extension (420) is operably coupled to said housing (406).

Clause 35—A handheld surgical instrument as recited in clause 31, wherein said displacement sensor (422) is a potentiometer.

Clause 36—A handheld surgical instrument as recited in clause 31, wherein said displacement sensor (422) is operationally coupled to said depth measurement extension (420) to provide said displacement signal (112, 212, 304) based on a position of said depth measurement extension (420).

Clause 37—A handheld surgical instrument as recited in clause 31, wherein said depth measurement extension (420) is a cannula.

Clause 38—A handheld surgical instrument as recited in clause 31, wherein said controller (410) writes to said memory device (412) at least a portion of said preceding velocity factored acceleration-related signal (312) within said first time interval (102, 202).

Clause 39—A handheld surgical instrument as recited in clause 31, further comprising a display (428), said display (428) configured to output a screw length indicator based on said bore hole (322) depth.

Clause 40—A handheld surgical instrument configured to determine bone thickness comprising: a displacement sensor (422) configured to provide a displacement signal (112, 212, 304) over a first time interval (102, 202), said first time interval (102) being bounded by an initial time (Ti) and a final time (Tf), said first time interval (102) corresponding to a drilling process; a controller (410), operably connected to said displacement sensor (422) to receive said displacement signal (112, 212, 304); a memory device (412) operably connected to a controller (410), where said memory device (412) is configured to store data; wherein said controller (410) is configured to: determine a preceding velocity-related signal (306) from said displacement signal (112, 212, 304) over a second time interval (104, 204), where said second time interval (104, 204) is at least a portion of said first time interval (102, 202); determine a succeeding velocity-related signal (308) over a third time interval (106, 206), where said third time interval (106, 206) beings within said first time interval (102, 202), said second time interval (104, 204) preceding said third time interval (106, 206); determine a first acceleration-related signal (136, 236, 310) over a fourth time interval (108, 208) based on said displacement signal (112, 212, 304), where said fourth time interval (108, 208) is at least a portion of the second time interval (104, 204) and at least a portion of the third time interval (106, 206); determine a preceding velocity acceleration-related signal (312) over said fourth time interval (108, 208) based on said preceding velocity-related signal (306) and said first acceleration-related signal (136, 236, 310); determine a soft-bone factored acceleration (318) for said fourth time interval (108, 208) based on said preceding velocity acceleration-related signal (312) over said second time interval (104, 204) and said succeeding velocity-related signal (308) over a third time interval (106, 206); determine a breakthrough time (Tb) of the drill bit through a distal cortical wall of the bone within said first time interval (102, 202) based on said soft-bone factored acceleration signal (318); and determine a bore hole depth (322) from a starting displacement from said displacement signal (112, 212, 304) and a breakthrough displacement (130, 230) from said displacement signal (112, 212, 304) at said breakthrough time (Tb).

Clause 41—A handheld surgical instrument as recited in clause 40, wherein said handheld surgical instrument comprises a housing (406).

Clause 42—A handheld surgical instrument as recited in clause 40, wherein said handheld surgical instrument comprises a motor (414) positioned within said housing 406).

Clause 43—A handheld surgical instrument as recited in clause 40, wherein said handheld surgical instrument comprises a depth measurement extension (420), where said depth measurement extension (420) is operably coupled to said housing (406).

Clause 44—A handheld surgical instrument as recited in clause 40, wherein said displacement sensor (422) is a potentiometer.

Clause 45—A handheld surgical instrument as recited in clause 40, wherein said displacement sensor (422) is operationally coupled to said depth measurement extension (420) to provide said displacement signal (112, 212, 304) based on a position of said depth measurement extension (420).

Clause 46—A handheld surgical instrument as recited in clause 40, wherein said depth measurement extension (420) is a cannula.

Clause 47—A handheld surgical instrument as recited in clause 40, further comprising a display (428), said display (428) configured to output a screw length (324) indicator based on said bore hole (322) depth (322).

Clause 48—A tool configured to determine a bore hole depth in bone, said tool comprising: a depth measurement extension (420), where said depth measurement extension (420) is coupled to a housing (406), a displacement sensor (422), operably connected to said depth measurement extension (420) such that said displacement sensor (422) is configured to provide a displacement signal (112, 212, 304) over a first time interval (102, 202) upon movement of said depth measurement extension (420), said first time interval (102, 202) being bounded by an initial time (Ti) and a final time (Tf), said first time interval (102) corresponding to a drilling process; a controller (410), operably connected to said displacement sensor (422) to receive said displacement signal (112, 212, 304); a memory device (412) operably connected to a controller (410), where said memory device (412) is configured to store data; wherein said controller (410) is configured to: determine a preceding velocity-related signal (306) from said displacement signal (112, 212, 304) over a second time interval (104, 204), where said second time interval (104, 204) is at least a portion of said first time interval (102, 202); determine a succeeding velocity-related signal (308) over a third time interval (106, 206) based on said displacement signal (112, 212, 304), said third time interval (106, 206) being within said first time interval (102, 202), said second time interval (104, 204) preceding said third time interval (106, 206); determine a first acceleration-related signal (136, 236, 310) within a fourth time interval (108, 208), said fourth time interval (108, 208) including at least a portion of said second time interval (104, 204) and said third time interval (106, 206) based on said displacement signal (112, 212, 304), wherein said fourth time interval (108, 208) includes only the at least one forward drilling time interval (126, 226) proceeding from the last point of furthest position; determine a preceding velocity factored acceleration-related signal (312) for said fourth time interval (108, 208) based on said first acceleration-related signal (136, 236, 310) and said preceding velocity-related signal (306); identify an acceleration cycle block (138, 238, 314) within said portion of first acceleration-related signal (136, 236, 310), said acceleration cycle block (138, 238, 314) corresponding to a fifth time interval (110, 210) where increasing acceleration-related signal values precede decreasing acceleration related signal values; determine a maximum acceleration in the acceleration cycle block (316) within the fifth time interval (110, 210); determine a soft-bone factored acceleration (318) for said fifth time interval (110, 210) based on said preceding velocity factored acceleration-related signal (312) and said succeeding velocity-related signal (308) at maximum acceleration; determine a maximum soft-bone factored acceleration (318) within said fourth time interval (108, 208); determine a breakthrough time (Tb) of the drill bit through a distal cortical wall of the bone within said first time interval (102, 202) as the time corresponding to the maximum soft-bone factored acceleration (318); and determine a depth of the bore hole (322) from a starting displacement from said displacement signal (112, 212 304) and a breakthrough displacement (130, 230) from said displacement signal (112, 212, 304) at said breakthrough time (Tb).

Clause—49 A tool as recited in clause 48, wherein said controller (410) writes to said memory device (412) at least a portion of said preceding velocity factored acceleration-related signal (312).

Clause 50—A tool as recited in clause 48, wherein said controller (410) writes to said memory device (412) at least a portion of said soft-bone factored acceleration signal (318).

Clause 51—A tool as recited in clause 48, wherein said depth measurement extension (420) is a cannula.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the examples is described above as having certain features, any one or more of those features described with respect to any example of the disclosure can be implemented in and/or combined with features of any of the other examples, even if that combination is not explicitly described. In other words, the described examples are not mutually exclusive, and permutations of one or more examples with one another remain within the scope of this disclosure.

Spatial and functional relationships between elements (for example, between controllers, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements.

As used herein, the phrase at least one of A, B, and C should be construed to mean a logical (A OR B OR C), using a non-exclusive logical OR, and should not be construed to mean "at least one of A, at least one of B, and at least one of C." The term subset does not necessarily require a proper subset. In other words, a first subset of a first set may be coextensive with (equal to) the first set.

In the figures, as may be applicable, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "controller" may be replaced with the term "circuit." The term "controller" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The controller may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The controller may communicate with other controllers using the interface circuit(s). Although the controller may be depicted in the present disclosure as logically communicating directly with other controllers, in various implementations the controller may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the controller may be distributed among multiple controllers that are connected via the communications system. For example, multiple controllers may implement the same functionality distributed by a load balancing system. In a further example, the functionality of the controller may be split between a server (also known as remote, or cloud) controller and a client (or, user) controller.

Some or all hardware features of a controller may be defined using a language for hardware description, such as IEEE Standard 1364-2005 (commonly called "Verilog") and IEEE Standard 1076-2008 (commonly called "VHDL"). The hardware description language may be used to manufacture and/or program a hardware circuit. In some implementations, some or all features of a controller may be defined by a language, such as IEEE 1666-2005 (commonly called "SystemC"), that encompasses both code, as described below, and hardware description.

The term code, as used above, may include software, firmware, and/or microcode, and may refer to programs, routines, functions, classes, data structures, and/or objects. The term shared processor circuit encompasses a single processor circuit that executes some or all code from multiple controllers. The term group processor circuit encompasses a processor circuit that, in combination with additional processor circuits, executes some or all code from one or more controllers. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple controllers. The term group memory circuit encompasses a memory circuit that, in combination with additional memories, stores some or all code from one or more controllers.

The term memory circuit, as may be applicable, is a subset of the term computer-readable medium. The term computer-readable medium, as may be used herein, does not encompass transitory electrical or electromagnetic signals propagating through a medium (such as on a carrier wave); the term computer-readable medium may therefore be considered tangible and non-transitory. Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements, as may described above, serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript °, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

The invention claimed is:

1. A measurement module comprising:
a displacement sensor configured to provide a displacement signal over a first time interval, the first time interval being bounded by an initial time and a final time, the first time interval corresponding to a drilling process;
a controller operably connected to the displacement sensor to receive the displacement signal; and
a memory device operably connected to the controller, where the memory device is configured to store data;
wherein the controller is configured to:

determine a preceding velocity-related signal from the displacement signal over a second time interval, where the second time interval is at least a portion of the first time interval;

determine a first acceleration-related signal over a third time interval based on the displacement signal, the third time interval being within the first time interval, where the third time interval is after the second time interval;

determine a preceding velocity factored acceleration-related signal for the third time interval based on the first acceleration-related signal and the preceding velocity-related signal; and determine a breakthrough time of a drill bit through a cortical wall of a bone within the first time interval based on the preceding velocity factored acceleration-related signal.

2. The measurement module of claim 1, wherein the controller is further configured to determine a bore hole depth based on the breakthrough time and the displacement signal.

3. The measurement module of claim 1, wherein the displacement sensor comprises a potentiometer.

4. The measurement module of claim 1, wherein the controller is configured to write to the memory device at least a portion of the preceding velocity factored acceleration-related signal within the first time interval.

5. The measurement module of claim 1, further comprising a first housing for supporting the displacement sensor.

6. The measurement module of claim 5, further comprising a depth measurement extension operably coupled to the first housing, wherein the displacement sensor is operably coupled to the depth measurement extension and configured to generate displacement signals responsive to movement of the depth measurement extension relative to the first housing.

7. A handheld surgical instrument comprising:
the measurement module of claim 5, and
a second housing supporting a motor, the second housing configured to be removably coupled to the first housing.

8. A measurement module comprising:
a displacement sensor configured to provide a displacement signal over a first time interval, the first time interval being bounded by an initial time and a final time, the first time interval corresponding to a drilling process;
a controller, operably connected to the displacement sensor to receive the displacement signal; and
a memory device operably connected to the controller, where the memory device is configured to store data;
wherein the controller is configured to:
determine a soft-bone factored acceleration signal based on a preceding velocity acceleration-related signal and a succeeding velocity-related signal; and
determine a breakthrough time of a drill bit through a cortical wall of a bone within the first time interval based on the soft-bone factored acceleration signal.

9. The measurement module of claim 8, wherein the controller is further configured to determine a bore hole depth based on the breakthrough time and the displacement signal.

10. The measurement module of claim 8, wherein the displacement sensor comprises a potentiometer.

11. The measurement module of claim 8, wherein the controller is configured to write to the memory device at least a portion of the soft-bone factored acceleration signal within the first time interval.

12. The measurement module of claim 8, further comprising a first housing for supporting the displacement sensor.

13. The measurement module of claim 12, further comprising a depth measurement extension operably coupled to the first housing, wherein the displacement sensor is operably coupled to the depth measurement extension and configured to generate displacement signals responsive to movement of the depth measurement extension relative to the first housing.

14. A handheld surgical instrument comprising:
the measurement module of claim 12, and
a second housing supporting a motor, the second housing configured to be removably coupled to the first housing.

15. A measurement module comprising:
a displacement sensor configured to provide a displacement signal over a first time interval, the first time interval being bounded by an initial time and a final time, the first time interval corresponding to a drilling process; and
a controller operably connected to the displacement sensor to receive the displacement signal, wherein the controller is configured to:
identify an acceleration cycle block, the acceleration cycle block corresponding to a second time interval within the first time interval where increasing acceleration-related signal values precede decreasing acceleration related signal values;
determine a maximum acceleration in the acceleration cycle block within the second time interval;
determine a soft-bone factored acceleration signal for the second time interval based on a preceding velocity factored acceleration-related signal and a succeeding velocity-related signal at maximum acceleration;
determine a maximum soft-bone factored acceleration; and
determine a breakthrough time of a drill bit through a cortical wall of a bone based on the maximum soft-bone factored acceleration.

16. The measurement module of claim 15, wherein the controller is further configured to determine a bore hole depth based on the breakthrough time and the displacement signal.

17. The measurement module of claim 15, wherein the displacement sensor comprises a potentiometer.

18. The measurement module of claim 15, further comprising a first housing for supporting the displacement sensor.

19. The measurement module of claim 18, further comprising a depth measurement extension operably coupled to the first housing, wherein the displacement sensor is operably coupled to the depth measurement extension and configured to generate displacement signals responsive to movement of the depth measurement extension relative to the first housing.

20. A handheld surgical instrument comprising:
the measurement module of claim 18, and
a second housing supporting a motor, the second housing configured to be removably coupled to the first housing.

* * * * *